(12) United States Patent
Schechner et al.

(10) Patent No.: US 8,813,364 B2
(45) Date of Patent: Aug. 26, 2014

(54) METHODS FOR MAKING LAYERED DENTAL APPLIANCES

(75) Inventors: Gallus Schechner, Seefeld (DE); Michael Jahns, Gilching (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/512,037

(22) PCT Filed: Dec. 8, 2010

(86) PCT No.: PCT/US2010/059350
§ 371 (c)(1), (2), (4) Date: May 25, 2012

(87) PCT Pub. No.: WO2011/075349
PCT Pub. Date: Jun. 23, 2011

(65) Prior Publication Data
US 2012/0285019 A1    Nov. 15, 2012

Related U.S. Application Data

(60) Provisional application No. 61/287,725, filed on Dec. 18, 2009.

(51) Int. Cl.
| | | |
|---|---|---|
| *A61C 5/10* | (2006.01) |
| *B23P 13/00* | (2006.01) |
| *B23P 25/00* | (2006.01) |
| *A61C 8/00* | (2006.01) |
| *A61C 13/08* | (2006.01) |
| *A61C 5/00* | (2006.01) |
| *A61C 5/08* | (2006.01) |
| *A61C 13/20* | (2006.01) |
| *A61C 13/10* | (2006.01) |
| *A61C 13/00* | (2006.01) |
| *A61C 13/09* | (2006.01) |

(52) U.S. Cl.
CPC ............. *A61C 13/0004* (2013.01); *A61C 13/09* (2013.01); *A61C 13/0022* (2013.01)
USPC ...... 29/896.11; 29/458; 29/896.1; 433/201.1; 433/202.1; 433/215; 433/217.1; 433/218; 433/223; 264/16; 264/17; 264/18; 264/19

(58) Field of Classification Search
USPC ................ 29/896.1, 458, 896.11; 433/201.1, 433/202.1, 203.1, 215, 217.1, 218, 223; 264/16–20
See application file for complete search history.

(56) References Cited

U.S. PATENT DOCUMENTS 3,810,773 A    5/1974    Shannon
4,078,310 A    3/1978    Horger
(Continued)

FOREIGN PATENT DOCUMENTS

CN    1257851    6/2000
CN    1594196    3/2005
(Continued)

OTHER PUBLICATIONS

K. Prabhakaran, "Casting of Alumina Using Boehmite as a Binder", Journal Eur. Ceram. Soc., 19 (1999) 2875-2881.
(Continued)

*Primary Examiner* — Essama Omgba
*Assistant Examiner* — Darrell C Ford
(74) *Attorney, Agent, or Firm* — Nicole J. Einerson

(57) ABSTRACT

Methods for making a layered dental appliance. Some methods can include providing a solid structure (e.g., a die or a dental core, such as a fully sintered ceramic dental core) having a desired outer shape, and applying a first slurry to the solid structure to form a first free form layer on the solid structure. The method can further include solidifying the first free form layer on the solid structure, and machining the solidified first free form layer to a desired shape to form a first article comprising the solid structure and a first shaped layer. The method can further include applying, solidifying, and machining a second layer in a similar way to form a second article comprising the solid structure, the first shaped layer, and a second shaped layer. In some methods, the free form layers are not exposed to a high temperature prior to being machined.

21 Claims, 1 Drawing Sheet

(56) References Cited

U.S. PATENT DOCUMENTS

| | | | |
|---|---|---|---|
| 4,115,487 A | 9/1978 | Rockett | |
| 4,153,403 A * | 5/1979 | Schneider | 425/159 |
| 4,155,964 A * | 5/1979 | Aronow | 264/13 |
| 4,246,086 A | 1/1981 | Hennicke | |
| 4,321,042 A | 3/1982 | Scheicher | |
| 4,560,666 A * | 12/1985 | Yoshida et al. | 501/5 |
| 4,937,928 A | 7/1990 | Van der Zel | |
| 5,000,940 A * | 3/1991 | Staples et al. | 424/49 |
| 5,028,362 A | 7/1991 | Janney | |
| 5,204,055 A | 4/1993 | Sachs | |
| 5,342,201 A | 8/1994 | Oden | |
| 5,501,600 A | 3/1996 | Johnson | |
| 5,697,043 A | 12/1997 | Baskaran | |
| 5,849,068 A * | 12/1998 | Hofmann et al. | 106/35 |
| 5,975,905 A * | 11/1999 | Kim et al. | 433/222.1 |
| 5,989,031 A | 11/1999 | Kura | |
| 6,048,205 A * | 4/2000 | Wright | 433/202.1 |
| 6,059,949 A | 5/2000 | Gal-Or | |
| 6,126,732 A * | 10/2000 | Hofmann et al. | 106/35 |
| 6,395,202 B1 | 5/2002 | Nagel | |
| 6,465,541 B2 * | 10/2002 | Bretscher et al. | 523/117 |
| 6,648,645 B1 | 11/2003 | MacDougald | |
| 6,740,267 B1 | 5/2004 | Sekino | |
| 6,866,929 B2 * | 3/2005 | Kodas et al. | 428/357 |
| 6,869,552 B2 | 3/2005 | Glidewell | |
| 6,955,776 B1 | 10/2005 | Feenstra | |
| 7,086,863 B2 | 8/2006 | Van der Zel | |
| 7,181,862 B2 | 2/2007 | Boara | |
| 7,236,842 B2 | 6/2007 | Kopelman | |
| 7,384,470 B2 | 6/2008 | Binkle | |
| 7,446,057 B2 | 11/2008 | Bietsch | |
| 7,536,234 B2 | 5/2009 | Kopelman | |
| 7,689,310 B2 | 3/2010 | Kopelman | |
| 7,806,694 B2 * | 10/2010 | Brodkin et al. | 433/201.1 |
| 2002/0022677 A1 * | 2/2002 | Teramae et al. | 523/113 |
| 2002/0157419 A1 | 10/2002 | Ganguli | |
| 2003/0222366 A1 | 12/2003 | Stangel | |
| 2004/0026833 A1 * | 2/2004 | Culler et al. | 264/461 |
| 2004/0245663 A1 | 12/2004 | MacDougald | |
| 2006/0008777 A1 | 1/2006 | Peterson | |
| 2006/0204542 A1 * | 9/2006 | Zhang et al. | 424/423 |
| 2006/0257824 A1 | 11/2006 | Pfeiffer | |
| 2006/0275738 A1 * | 12/2006 | Flanagan | 433/215 |
| 2007/0092853 A1 | 4/2007 | Liu | |
| 2008/0131841 A1 | 6/2008 | Taub | |
| 2008/0206460 A1 | 8/2008 | Rhoades | |
| 2008/0241788 A1 | 10/2008 | Bauer | |
| 2008/0302135 A1 | 12/2008 | Costa | |
| 2008/0318189 A1 | 12/2008 | Brodkin | |
| 2009/0004630 A1 * | 1/2009 | van der Zel et al. | 433/223 |
| 2009/0081616 A1 * | 3/2009 | Pfeiffer | 433/215 |
| 2009/0115084 A1 * | 5/2009 | Moon | 264/16 |
| 2009/0233258 A1 | 9/2009 | Luthardt | |
| 2009/0311649 A1 | 12/2009 | Detje | |
| 2009/0311650 A1 | 12/2009 | Stephan | |
| 2010/0025874 A1 | 2/2010 | Apel | |
| 2010/0035215 A1 | 2/2010 | Brodkin | |
| 2010/0167238 A1 | 7/2010 | Kopelman | |
| 2010/0233655 A1 | 9/2010 | Karim | |
| 2010/0248189 A1 * | 9/2010 | Burger et al. | 433/203.1 |
| 2012/0193823 A1 * | 8/2012 | Goetzinger et al. | 264/16 |
| 2013/0180110 A1 * | 7/2013 | Schechner et al. | 29/896.1 |
| 2013/0209961 A1 * | 8/2013 | Rubbert et al. | 433/175 |
| 2013/0295522 A1 * | 11/2013 | Chu et al. | 433/208 |

FOREIGN PATENT DOCUMENTS

| | | |
|---|---|---|
| DE | 19922870 | 7/2000 |
| EP | 0311214 | 4/1989 |
| EP | 0455854 | 11/1991 |
| EP | 0943296 | 9/1999 |
| EP | 1250895 | 10/2002 |
| EP | 1258456 | 11/2002 |
| EP | 1252867 | 7/2005 |
| EP | 1561433 | 8/2005 |
| EP | 1661866 | 5/2006 |
| EP | 1972321 | 9/2008 |
| EP | 1992302 | 11/2008 |
| GB | 418160 | 10/1934 |
| JP | 01-258920 | 10/1989 |
| JP | 2004-298599 | 10/2004 |
| WO | WO 94/27517 | 12/1994 |
| WO | WO 97/44291 | 11/1997 |
| WO | WO 01/13814 | 3/2001 |
| WO | WO 01/53225 | 7/2001 |
| WO | WO 03/093195 | 11/2003 |
| WO | WO 2004/063105 | 7/2004 |
| WO | WO 2006/120255 | 11/2006 |
| WO | WO 2007/028787 | 3/2007 |
| WO | WO 2007/051447 | 5/2007 |
| WO | WO 2009/070469 | 6/2009 |
| WO | WO 2010/039910 | 4/2010 |
| WO | WO 2010/053698 | 5/2010 |
| WO | WO 2010/074890 | 7/2010 |
| WO | WO 2010/110650 | 9/2010 |
| WO | WO 2010/110662 | 9/2010 |
| WO | WO 2011/041182 | 4/2011 |
| WO | WO 2011/041193 | 4/2011 |
| WO | WO 2011/041194 | 4/2011 |
| WO | WO 2011/075349 | 6/2011 |

OTHER PUBLICATIONS

Ullmann's Encyclopedia of Industrial Chemistry (2008), Chapter Silica, Section 4.1 and 5.2.
Ullmann's Encyclopedia of Industrial Chemistry (2005) Chapter Inorganic Polymers, pp. 1-39.
Beuer et al., "High-Strength CAD/CAM-fabricated veneering material sintered to zirconia copings—A new fabrication mode for all-ceramic restorations"; Dental Materials 25 (2009) 121-128.
International Search Report PCT/US2010/059350; Mar. 18, 2011, 5 pages.
Buckley, "Sol-Gel Preparation of Silica Gels", M. J. Chem, Ed 1994, 71(7), 599; 9 pgs.

* cited by examiner

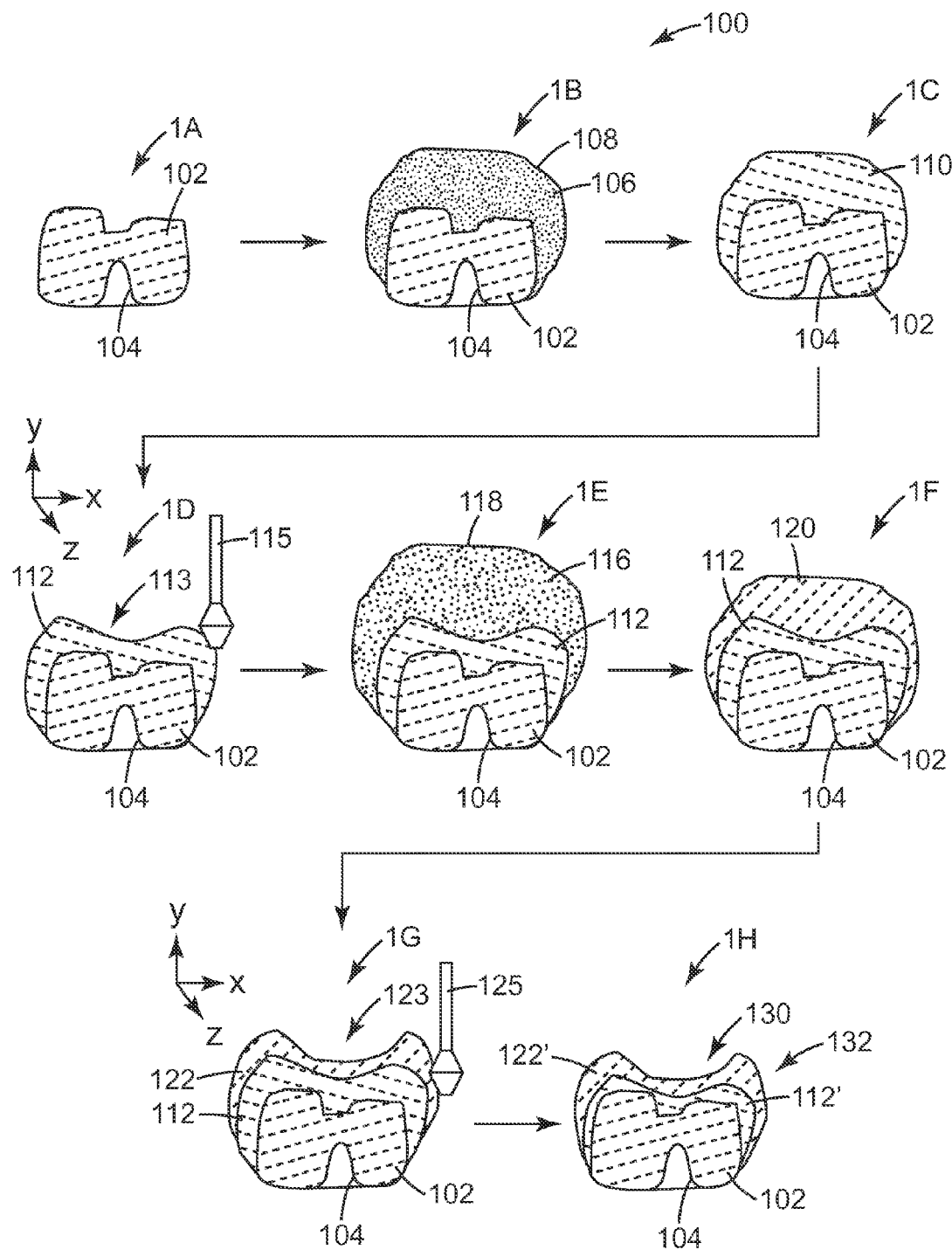

METHODS FOR MAKING LAYERED DENTAL APPLIANCES

RELATED APPLICATIONS

This is a national stage filing under 35 U.S.C. 371 of PCT/US2010/059350, filed Dec. 8, 2010, which claims priority to U.S. Provisional Application No. 61/287,725, filed Dec. 18, 2009, the disclosure of which is incorporated by reference in its entirety herein.

The present disclosure is generally directed to systems and methods for making dental appliances, and particularly, to systems and methods for making layered dental appliances.

BACKGROUND

Some existing dental restorations, such as crowns, formed of glass and/or glass ceramic materials are produced by grinding bodies of compacted and heat treated glass and/or glass ceramic particles. Such bodies can be produced by mechanical compacting (e.g. uniaxial pressing) of inorganic powders often together with an organic binder first. The shape of the resulting compacted body can be limited to the shape of the compacting tool used. In some cases, cylindrical or cuboid shaped bodies can be obtained. Such compacted bodies can then undergo a heat treatment to increase the mechanical strength of the compacted bodies. Such a heat treatment can take place at a temperature that causes at least partial sintering of the powder. During such a sintering step, the density of the body of compacted powder can be increased. The resulting compacted and heat treated bodies can then be adhesively fixed in a frame or attached to a holder to prepare them for grinding to a desired shape (e.g. a dental crown or dental facing). The ground bodies can then be removed from the frame. Machining of the compacted bodies which have not been heat treated may not be possible due to the low mechanical strength of the compacted powder.

In addition, in some existing dental systems, a core is milled and then sintered (e.g., to full density). A veneer can also be milled from a mill blank and fused to the core, for example, with a slurry forming an intermediate layer between the core and the veneer. The veneer can then be sintered to the core.

Moreover, in some existing dental systems, dental restorations, such as crowns, can be produced using a manual process of covering a core layer-by-layer with veneering slurries (e.g., using a small brush). Firing steps can be included after application of each layer.

Finally, in some existing systems, solid free form fabrication methods employing additive processes, such as three-dimensional printing, have been used to form various dental restorations. For example, in some cases, direct or indirect additive deposition or printing methods are used to build up a dental restoration on a die or in a mold.

SUMMARY

Some aspects of the present disclosure provide a method for making a layered dental appliance. The method can include providing a dental core having a desired outer shape, and applying a slurry to the solid structure to form a first free form layer on the dental core. The method can further include solidifying the first free form layer on the dental core, and machining the solidified first free form layer to a desired shape to form a first article comprising the dental core and a first shaped layer.

Some aspects of the present disclosure provide a method for making a layered dental appliance. The method can include providing a solid structure having a desired outer shape, and applying a first slurry to the solid structure to form a first free form layer on the solid structure. The method can further include solidifying the first free form layer on the solid structure, and machining the solidified first free form layer to a desired shape to form a first article comprising the solid structure and a first shaped layer. The method can further include applying a second slurry to the first article to form a second free form layer, and solidifying the second free form layer on the first article. The method can further include machining the solidified second free form layer to a desired shape to form a second article comprising the solid structure, the first shaped layer and a second shaped layer.

Other features and aspects of the present disclosure will become apparent by consideration of the detailed description and accompanying drawings.

BRIEF DESCRIPTION OF THE DRAWINGS

FIG. 1 is a schematic flowchart of a method according to one embodiment of the present disclosure.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "supported," and "coupled" and variations thereof are used broadly and encompass both direct and indirect supports and couplings. Further, "connected" and "coupled" are not restricted to physical or mechanical connections or couplings. It is to be understood that other embodiments may be utilized, and structural or logical changes may be made without departing from the scope of the present disclosure.

The present disclosure generally relates to methods for making layered dental appliances, such as dental restorations. Some methods of the present disclosure can produce net-shape or near-net-shape dental appliances (e.g., restorations) via an iterative layering process (e.g., employing a sol-gel process), wherein each layer can be individually machined prior to the next layer being applied, without requiring that the layer to be machined is fired or sintered (e.g., pre-sintered), or otherwise exposed to high temperatures, prior to machining. Multiple layering and machining steps can be performed consecutively to achieve layered structures. The final layered structure can then be fired. The methods of the present disclosure are particularly useful for forming veneering layers, and particularly, for forming veneering layers on a fully sintered ceramic (e.g., zirconia) or metal dental core.

At least because the methods of the present disclosure do not require any sintering or firing to occur prior to the machining steps, the methods of the present disclosure can allow for machining of lower density articles, which can thereby (1) decrease the wear on machining tools; (2) can allow for the use of faster and more efficient milling techniques (e.g., as opposed to other machining techniques); and (3) can decrease the cycle time required to produce a finished dental appliance.

In some embodiments, a dental appliance such as a dental restoration, can be desired that not only meets the performance or material requirements but is also visually indistinguishable from adjacent natural tooth surfaces. A layered dental appliance can have improved aesthetics over a single layer or single material appliance, for example, if one or more layers toward the outer surface of the appliance are more translucent than inner layer(s), such that the appliance (e.g., restoration) more closely mimics the appearance of a natural tooth.

In some embodiments, the systems and methods of the present disclosure may not be performed in situ, or in a patient's mouth. Rather, in some embodiments, the systems and methods of the present disclosure can be employed in a laboratory setting, such as in a dental laboratory. That is, in some embodiments, the methods of the present disclosure can be referred to as lab-bench, desktop, or laboratory procedures. The methods also may be used directly in dental offices as so called "chair side" procedures.

Some methods of the present disclosure can include providing a solid structure (e.g., a dental core) having a desired outer shape that can form the innermost core of the resulting layered dental appliance. However, in some embodiments, the solid structure can actually be a fire-resistant die that can be removed from the final dental appliance to form, for example, a dental veneer or crown having a desired inner shape as well as a desired outer shape.

In some methods of the present disclosure, a first amount of a slurry can be applied to the solid structure to form a first free form layer. The first layer can be solidified, for example by drying (e.g., at a low temperature) and/or by solidifying via a low-temperature chemical reaction (e.g., a sol-gel reaction). The solidified first layer (e.g., wet or dry) can then be machined to a desired shape (e.g., a complex three-dimensional shape including varying thicknesses, as desired) using subtractive machining processes. A second amount of a slurry (which can be the same formulation or a different formulation from the slurry used to form the first layer) can then be applied to the first shaped layer to form a second free form layer. The second free form layer can be solidified similar to the first layer, and the solidified second layer can then be machined to a desired shape using subtractive machining processes, and the shape of the second layer can be the same as or different from the shape of the first layer. This iterative layering and machining process can then continue until a desired amount of layers have been formed on the solid structure, each layer having the desired aesthetics, and each layer not needing to have been pre-sintered or fired prior to being shaped. The resulting layered article can then be fired to form a finished layered dental appliance. The solid structure can form a portion of the finished dental appliance, or the solid structure can be removed (e.g., in embodiments in which the solid structure is a fire-resistant die).

Some existing methods for forming dental appliances (or portions thereof) include building up the material by additive methods, such as three-dimensional printing ("3D printing"), which can include, for example, rapid prototyping. In some cases, it can be very difficult to control a 3D printing head close to a surface (such as the outer surface of a solid structure, e.g., the dental core) without crashing the 3D printing into the surface. In other existing methods, individual dental cores and dental veneers can be separately and individually fabricated and then fused together to form a final dental appliance. Unlike the 3D printing, the methods of the present disclosure avoid the potential problems associated with 3D printing and allow for facile application methods, followed by machining steps that can create very specific layers having predetermined and unique shapes, thicknesses, and/or optical or aesthetic properties (e.g., translucence, color, etc.), without the need to expose the layer to high temperatures (e.g., sintering) prior to being machined. The methods of the present disclosure also avoid the need for any final joining or fusing steps of separate components. The methods of the present disclosure provide full freedom of design. For example, a specific desired dentin structure of an anterior tooth (mamelons) can be machined (e.g., milled) in a dentin-simulating layer, and can be covered by dipping into a slurry adapted to simulate enamel (e.g., when it dries and hardens). The enamel layer can be allowed to solidify to a strength suitable for machining, and then a specific enamel structure can be machined (e.g., milled).

The term "dental appliance" generally refers to any dental or orthodontic restoration, dental mill blank, prosthetic device, or combination thereof. The appliance may be a finished appliance ready for introduction into the mouth of a patient, an appliance without the finishing (e.g. without stains) but with its final shape (i.e., a "net shape" appliance), or it may be a preformed or near-final dental appliance (i.e., a "near-net shape" appliance), which can be subjected to further processing before use, such as a dental mill blank.

The phrase "dental mill blank" generally refers to a solid block of material from which a desired product (e.g., a dental restoration) can be machined. A dental mill blank may have a size of about 10 mm to about 30 mm in two dimensions. For example, a dental mill blank may have a diameter in that range, and may be of a certain length in a third dimension. A blank for making a single crown may have a length of about 15 mm to about 30 mm, and a blank for making bridges may have a length of about 40 mm to about 80 mm. In some embodiments, a blank used for making a single crown can have a diameter of about 24 mm and a length of about 19 mm. In some embodiments, a blank used for making bridges can have a diameter of about 24 mm and a length of about 58 mm.

The term "machining" generally refers to shaping a material by a machine, and can include, but is not limited to one or more of milling, grinding, cutting, carving, or a combination thereof. In some cases, milling can be faster and more cost-effective than grinding. Machining also generally refers to "subtractive" processes, in which material is removed in order to form a desired shape or structure. Subtractive processes are in contrast to "additive" processes in which material is applied, added, or "built-up" to form a desired shape or structure.

Particularly, machining can include subtractive CAD/CAM processes, in which a digital workflow is used to determine the desired shape or features (e.g., in three dimensions), and/or to guide the machining process to remove material in order to form the desired shape. By way of example, in some embodiments, a specially designed tooth-shape (e.g., a positive of the tooth-shape and/or a negative of the tooth-shape) can be produced by a digital workflow. Such a digital workflow can include scanning a patient's mouth to develop a model for the desired dental appliance. Such scanning can be performed using an optical scanner that is coupled to a computer-aided design (CAD) system that functions in conjunction with a computer-integrated manufacturing (CIM) or computer-aided manufacturing (CAM) system. Such a CAD/CAM system is available, for example, under the trade designation LAVA™ from 3M ESPE AG (Seefeld, Germany).

The phrase "dental workpiece" generally refers to a dental appliance which has been further processed (e.g. by machining) to obtain an intentionally shaped product. A dental workpiece can be further processed (e.g. by sintering) or used as such. In methods of the present disclosure, each layering step can be referred to as forming a dental workpiece that has an intentional shape. This intermediate workpiece is sometimes referred to herein as simply an "article." When all of the desired layers have been applied and machined to a unique shape, the final dental workpiece can be sintered or otherwise further processed to form a final layered dental appliance.

The phrase "dental restoration" is generally used to refer to any restoration that can be used in the dental field, including, but not limited to, crowns, partial crowns, inlays, onlays, abutments, bridges (e.g., including 2-part, 3-part, 4-part, 5-part or 6-part bridges), implants, other suitable dental articles, and combinations thereof. The dental restoration can include a three-dimensional inner and outer surface including convex and concave structures. Compared to other ceramic articles, such as pottery or paving stones, dental restorations can be relatively small and can include filigree. The thickness of a dental restoration can vary from very thin, for example at its edges and rims (e.g., less than about 0.1 mm) to considerably thick, for example, in the biting, or occlusal, area (e.g., up to about 7 mm). In some embodiments, the thickness of a dental restoration ranges from 0.3 mm to 0.5 mm.

In some embodiments, the dental restoration can comprise or consist essentially of a glass; glass ceramic; polycrystalline ceramic material, for example, comprising alumina (e.g., $Al_2O_3$), zirconia ($ZrO_2$), partly or fully stabilized zirconia (e.g., Yttrium-stabilized zirconia), titanium dioxide ($TiO_2$), high-strength oxides of the elements of the main groups II, III and IV and the subgroups III and IV, and their mixtures; metals, metal alloys, precious metals, precious metal alloys, or combinations thereof (e.g., cobalt alloys, such as cobalt-chromium, titanium alloys, gold/platinum/palladium alloys, etc., and combinations thereof); and combinations thereof. In some embodiments, the dental restoration can include at least two layers, for example, a dental core (or dental framework) and a dental veneer.

The phrase "dental core" or "dental framework" generally refers to a solid structure that can be pre-fabricated or at least partially pre-fabricated and then used as the innermost core or center layer of the layered dental appliance of the present disclosure. For example, in some embodiments, the dental core can be adapted to be coupled to or to fit over one or more of a tooth stump, an implant abutment, or the like, or combinations thereof.

The phrase "solid structure" generally refers to a solid object that can provide suitable support for at least the layering and machining steps of methods of the present disclosure. In some embodiments, the solid structure includes a dental core that forms a portion of the resulting dental appliance. In some embodiments, the solid structure includes a die (e.g., formed of a fire-resistant material) that can be used to support the dental appliance throughout its fabrication steps, but which is eventually removed to form a dental appliance having a cavity therein (e.g., having a desired inner shape) that is configured to fit onto a tooth stump, an implant, or the like, or combinations thereof.

The phrase "dental veneer" generally refers to a structure formed of one or more layers that can be coupled (e.g., fused) to or built upon another structure (e.g., a dental core) for color, aesthetics, texture, surface properties, etc., and, in some embodiments, to mimic the appearance of a natural tooth.

A dental core (sometimes referred to as a "dental framework") and a dental veneer can each include a three-dimensional inner and outer surface including convex and concave structures. The outer surface of the dental core can correspond to an inner surface of the dental veneer. The inner surface of the dental core can correspond to an outer surface of a prepared tooth stump, or implant abutment, whereas the outer surface of the dental veneer can correspond to the desired (e.g., final) dental restoration.

Dental cores or frameworks can be made of or comprise at least one of a ceramic, a metal, a metal alloy, a precious metal, a precious metal alloy, and combinations thereof. Examples of ceramics can include, but are not limited to, alumina (e.g., $Al_2O_3$); zirconia ($ZrO_2$); partly or fully stabilized zirconia (e.g., Yttrium-stabilized zirconia); titanium dioxide ($TiO_2$); high-strength oxides of the elements of the main groups II, III and IV and the subgroups III and IV, and combinations thereof; and combinations thereof. Examples of metals, metal alloys, precious metals, and precious metal alloys can include, but are not limited to, cobalt alloys (e.g., cobalt-chromium), titanium alloys, gold/platinum/palladium alloys, and combinations thereof.

Compared to other framework such as pottery or paving stones, dental cores or framework can be small and filigree, and of high strength. The thickness of the dental framework can vary from very thin, e.g. at the edges and rims (below about 0.1 mm) to considerably thick, e.g. in the biting area (up to about 7 mm).

In some embodiments, the dental core on which additional layers can be formed according to the methods of the present disclosure can be pre-sintered or finally sintered.

Dental veneers can include one or more layers that would be coupled (e.g., fused) to or built upon an inner core or center of a dental appliance. Dental veneers can also be small and filigree objects. The strength of dental veneers, however, can be less compared to dental frameworks. Dental veneers can be made of or comprise glass and/or glass ceramic materials. Examples of suitable glass materials include, but are not limited to, silica ($SiO_2$) in combination with one or more of alumina ($Al_2O_3$), potassium oxide ($K_2O$), sodium oxide ($Na_2O$), etc., and combinations thereof. Examples of suitable glass ceramic materials include, but are not limited to a material having a glass fraction comprising silica ($SiO_2$) in combination with one or more of alumina ($Al_2O_3$), potassium oxide ($K_2O$), sodium oxide ($Na_2O$), etc., and combinations thereof, and a crystalline fraction comprising e.g. leucite, lithium disilicate, etc., and combinations thereof.

In some embodiments, it can be important to match the coefficient of thermal expansion (CTE) of the dental core with that of a dental veneer (or a portion of the dental veneer). Otherwise, in some cases, the veneer and the core may not be fused correctly during firing which might lead to failure of the restoration. In some embodiments, glass itself (e.g., including some of the formulations listed above) may match that of zirconia. In some embodiments, for example, when a dental core comprises metal, which tend to have a higher CTE, a crystalline material (e.g., leucite) may need to be added to the glass forming the veneer. Adding leucite to glass can raise the CTE of the glass, and can also improve the mechanical strength of the glass, but crystal materials other than leucite can also be used. The amount of leucite (or other crystal phase) to be added to the glass can depend on the material makeup of the dental core to which the dental veneer will be coupled (e.g., fused), because different metals and alloys have different CTEs. Alumina has a lower CTE compared to zirconia so the glass can be adapted in its composition to reach this lower CTE (e.g. Vita VM7 (VM9 can be used for zirconia, for example), Vita Zahnfabrik, Germany). Table 1 lists exemplary pairings of dental core and dental veneer materials. Table 1 is only intended to be illustrative and not limiting:

TABLE 1

Exemplary pairings of dental core and dental veneer materials

| Dental Core materials | Dental Veneer materials |
|---|---|
| Zirconia | glass (e.g., SiO2 with Al2O3, K2O, Na2O, etc.) |
| Alumina | glass (e.g., SiO2 with Al2O3, K2O, Na2O, etc.) |
| Metal | glass ceramic: glass fraction (e.g., SiO2 with Al2O3, K2O, Na2O, etc.) and crystalline fraction (e.g. leucite) |

The term "glass" generally refers to a hard, brittle, transparent solid. Examples of glasses can include, but are not limited to, soda-lime glass and borosilicate glass. A glass can include an inorganic product of fusion that has been cooled to a rigid condition without crystallizing. Some glasses contain silica as their main component and a certain amount of glass former.

The phrase "glass ceramic" generally refers to a material sharing many properties with both glass and more crystalline ceramics. It is formed as a glass, and then made to crystallize partly by heat treatment. The space between the crystallites is filled by the glassy matrix. Glass ceramics mainly refer to a mixture of alkali metal-, silicon-, and aluminium-oxides.

The term "ceramic" generally refers to an inorganic non-metallic material that can be produced by application of heat. Ceramics can be hard, porous and brittle and, in contrast to glasses or glass ceramics, can display an essentially purely crystalline structure.

A dental ceramic appliance (e.g., which can be used as the dental core) can be classified as "pre-sintered" within the meaning of the present disclosure if the dental ceramic appliance has been treated with heat (e.g., a temperature ranging from about 900 to about 1100° C.) for about 1 to about 3 hours to such an extent that the raw breaking resistance (Weibull strength Sigma 0) of the dental ceramic appliance is within a range of about 15 to about 55 MPa or about 30 to about 50 MPa (measured according to the "punch on three ball test" (biaxial flexural strength) described in DIN EN ISO 6872, edition March 1999, with the following modifications: diameter of steel ball: 6 mm; diameter of support circle: 14 mm; diameter of flat punch: 3.6 mm; diameter of sample disc: 25 mm, thickness of sample disc: 2 mm; no grinding and polishing of samples.).

A pre-sintered dental ceramic appliance can include a porous structure and its density (e.g., which can be 3.0 g/cm$^3$ for an Yttrium stabilized $ZrO_2$ ceramic) can be less compared to a completely sintered or finally sintered (i.e., such that there will be no further sintering step) dental ceramic appliance (e.g., which can be 6.1 g/cm$^3$ for an Yttrium stabilized $ZrO_2$ ceramic). In some embodiments, the diameter of the pores can be in a range of about 50 nm to about 150 nm (corresponding to about 500 to about 1500 Å. In some embodiments, a pore diameter can be about 120 nm.

In some embodiments, pre-sintering of a glass and/or glass ceramic material can be effected in a temperature range of about 500 to about 750° C., and in some embodiments, from about 600° C. to about 700° C. However, in the present disclosure, the individual layers are generally formed without any pre-sintering or final sintering steps, until all of the desired layers have been formed, and the final appliance can be sintered. In some embodiments, the layers can be formed on a dental core that has been pre-sintered or fully sintered.

In some embodiments, sintering of a glass and/or glass ceramic material to full density can be effected in a temperature of at least about 700° C., and in some embodiments, at least about 750° C. In some embodiments, sintering to full density of a glass and/or glass ceramic material can be effected in a temperature of no greater than about 1000° C., and in some embodiments, no greater than about 950° C. In some embodiments, sintering to full density of a glass and/or glass ceramic material can be effected in a temperature range of from about 700° C. to about 1000° C., and in some embodiments, from about 750° C. to about 950° C., for example, for a period of about 1 to about 3 hours.

The term "sintering" generally refers to making objects from a powder by heating the material (e.g., below its melting point—"solid state sintering") until its particles adhere to each other. Sintering can cause the densification of a porous material to a less porous material (or a material having less cells) having a higher density. In some cases, sintering can also include changes of the material phase composition (e.g., a partial conversion of an amorphous phase toward a crystalline phase).

The terms "sintering" and "firing" are used interchangeably herein. A pre-sintered ceramic framework can shrink during a sintering step, that is, if an adequate temperature is applied. The sintering temperature to be applied depends on the material chosen. For example, for $ZrO_2$-based ceramics, a sintering temperature (e.g., for sintering to full density) can range from about 1200° C. to about 1600° C. In some embodiments, $Al_2O_3$-based ceramics can be sintered at a temperature ranging from about 1300° C. to about 1700° C.

The unit "cells per mm$^2$" is related to the number of cells present on a cross section of the sample to be analysed. A suitable test method is given in DIN 13925.

A "sol-gel reaction" is a wet-chemical technique (sometimes also referred to as "Chemical Solution Deposition") for the fabrication of materials starting either from a chemical solution or colloidal particles (e.g. nanoscale particle) to produce an integrated network (gel). In some embodiments, sol-gel precursors can include metal alkoxides and metal chlorides, which undergo hydrolysis and polycondensation reactions to form a colloid or sol, a system composed of solid particles (e.g., with sizes ranging from 1 nm to 1 μm) dispersed in a solvent. The sol can then evolve toward the formation of an inorganic continuous network containing a liquid phase (gel). Formation of a metal oxide can include connecting the metal centers with oxo (M-O-M) or hydroxo (M-OH-M) bridges, therefore generating metal-oxo or metal-hydroxo polymers in solution. A drying process can serve to remove the liquid phase from the gel thus forming a porous material. Afterwards, a thermal treatment (e.g., firing) may be performed in order to favor further polycondensation and enhance mechanical properties.

The phrase "porous material" can generally refer to a material comprising a partial volume that is formed by voids, pores, or cells in the technical field of ceramics.

The term "liquid" can generally refer to any solvent or liquid which is able to at least partially disperse or dissolve an inorganic binder of a slurry or mixture composition at ambient conditions (e.g. 23° C., 1013 mbar).

A composition or solution is "essentially or substantially free of" a certain component within the meaning of the present disclosure if the composition or solution does not contain said component as an essential feature. That is, such a component is not wilfully added to the composition or solution either as such or in combination with other components or as an ingredient of other components. In some embodiments, a composition being essentially free of a certain component usually contains the component in an amount of less than about 1 wt.-%, in some embodiments less than about 0.1 wt.-%, in some embodiments less than about 0.01 wt.-%, and in some embodiments less than about 0.001 wt.-

%, with respect to the whole composition. In some embodiments, "essentially or substantially free of" generally refers to the composition or solution not containing the component at all. However, sometimes the presence of a small amount of the component may not be avoidable, e.g. due to impurities being present in the raw materials used.

As mentioned above, some systems and methods of the present disclosure provide layered dental appliances having individually-shaped layers relatively quickly using an iterative layering and machining process. In some embodiments, a sol-gel reaction is employed in which a slurry or mixture is formed by combining:
  (i) a glass and/or glass ceramic powder;
  (ii) a liquid (e.g., water);
  (iii) a binder (e.g., an inorganic binder); and
  (iv) an activator (e.g., an acid or base).
In some embodiments, the slurry comprises components (i), (ii) and (iii), and the activator (component (iv)) is not added until just prior to applying the slurry to form a layer.

By providing a mixture comprising a liquid, a binder (e.g., an inorganic binder), and glass and/or glass ceramic powder or particles, a sol-gel process can be initiated resulting in a homogeneous distribution of the glass and/or glass ceramic powder or particles in an inorganic network. In contrast to this, blocks produced by uniaxial pressing sometimes are inhomogeneous with regard to density. This may be caused by an inhomogeneous pressure distribution in the pressing matrix.

Compared to a dental appliance manufactured by a pressing process and having insufficient strength unless it is pre-sintered, each layer obtainable according to the methods of the present disclosure has sufficient strength and can be machined without pre-sintering the layer. This can substantially decrease cycle time and increase the productivity of forming multilayered dental appliances, because, as explained in greater detail below with reference to FIG. 1, each layer of a dental appliance can be machined to a desired shape without adding the time-consuming step of pre-sintering the material prior to each machining step.

Moreover, machining is not limited to grinding only but can also be accomplished by milling as well. As outlined above, the strength of the intermediate articles (e.g., individual layers formed prior to any sintering process) obtained by the present disclosure is high enough that the dental appliance can be machined without a sintering step, but low enough that the dental appliance can be shaped by applying a more efficient (e.g. faster and cheaper) milling process.

Furthermore, by using an inorganic binder for creating an inorganic network instead of an organic binder, there can be less exhaust gases evaporating from the dental appliance during a later heating or sintering step. Organic binders can produce gases like carbon and/or nitrogen oxides. Examples of inorganic binders according to the present disclosure, if at all, only produce low boiling solvents like alcohols (e.g. methanol and ethanol) which typically evaporate during the drying step.

In addition and in contrast to pressing techniques which can be limited to specific shapes (e.g., cube and cylinder), the process of the present disclosure facilitates the manufacturing of complex shapes. Thus, objects with convex and/or concave structures can be manufactured.

Compared to pre-sintered dental appliances, the intermediate articles obtained by the process of the present disclosure (e.g., individual layers formed prior to any sintering process) can have a lower density. The lower density can facilitate machining of the layer (e.g. which can extend the service life of machining tools), and can also reduce the amount of waste that is produced during the shaping process.

Some methods of the present disclosure facilitate providing colored dental appliances. Coloring additives can be added very early in the process (e.g. when the mixture to be used for each layer is provided) and/or later on in the process (e.g. after each layer is dried/solidified, or after multiple layers have been applied and dried). If the coloring is to be done after the drying step, it can be done by using a coloring solution containing coloring additives (e.g. metal salts). If the coloring is to be determined by the respective slurry applied, it can be done by adding coloring additives (e.g. metal salts) to the slurry when it is produced.

Adding coloring additives at an early stage in the process, for example when providing the mixture to be used for each layer, can result in a homogenous distribution of the coloring additives throughout the resulting dental appliance, or throughout a layer of the resulting layered dental appliance.

The amount of inorganic binder precursor used can allow for adjusting or influencing the solidification time and the toughness of the solidified slurry. The amount of powder and water used can also allow for adjusting the density of the slurry.

FIG. 1 illustrates a schematic flowchart of a method 100 according to one embodiment of the present disclosure. The method 100 includes steps 1A-1H for forming a layered dental appliance. Steps 1A-1D are generally used to form a first shaped layer, and steps 1E-1G are generally used to form a second shaped layer.

In a first step 1A, a solid structure 102 can be provided. The solid structure 102 can include a recess or cavity 104 adapted to receive a tooth stump, a dental implant, a holder (or portion thereof) for machining, or combinations thereof. As mentioned above, in some embodiments, the solid structure 102 can be pre-sintered or fully sintered and can include a desired outer shape upon which other layers can be constructed. The solid structure 102 can also be metal. The solid structure 102 can either form the innermost layer or dental core of a resulting dental appliance, or the solid structure 102 can be a die that is removed from the resulting dental appliance, such that the resulting dental appliance includes, for example, a dental veneer. As a result, in some embodiments, the solid structure 102 can form a permanent portion of the resulting dental appliance, and in some embodiments, the solid structure 102 serves as a temporary support during the process for making a dental appliance. In embodiments employing a dental core as the solid structure 102 (i.e., that will form a portion of a resulting dental appliance), the dental core is generally fully sintered prior to being layered.

In a second step 1B, a first slurry 106 can be applied to the outer surface of the solid structure 102 to form a first free form layer 108. The first slurry 106 can be applied according to a variety of free-form methods, including, but not limited to, dipping, brushing, pouring or decanting, pipetting, delivering through a nozzle, spreading (e.g., with a spatula), other suitable mechanical deposition processes, or combinations thereof. In some embodiments, applying the first slurry 106 to the solid structure 102 can include rotating the solid structure 102 to facilitate achieving an even coverage. However, the first slurry 106 is generally not molded or otherwise formed to a prescribed shape in the application step. In addition, the first slurry 106 is generally not contained, constrained or restrained in any way in the application step. As a result, in some embodiments, the application of the first slurry 106 can be referred to as a "free-form" application process. Such a "free-form" application process can be less complex and can require fewer resources and equipment than other application or deposition processes.

In some embodiments, to facilitate applying the first slurry 106 and inhibiting the slurry 106 from immediately flowing off of the solid structure 102, the first slurry 106 can have a suitable viscosity. That is, in some embodiments, the first slurry 106 has a sufficient viscosity that is neither too low nor too high to facilitate application of the first slurry 106 to the outer surface of the solid structure 102. In some embodiments, if the viscosity of the first slurry 106 is too low, the first slurry 106 may not be appropriate for applying by methods other than dipping, such as decanting, delivering through a nozzle, etc.

In some embodiments, to ensure a viscosity appropriate for applying the first slurry 106, a rheological modifier can be added to the first slurry 106. For example, in embodiments in which the first slurry 106 is applied by methods other than dipping, it may be necessary to add a rheological modifier additive in order to adjust the viscosity of the first slurry 106.

The phrase "free form layer" can generally refer to a layer that does not have a prescribed or pre-determined shape, and that is generally not formed by any molding or casting procedures. However, in the sense of the present disclosure, the inner shape of a layer can be defined by the solid structure 102 to which the layer is applied.

In a third step 1C, the first free form layer 108 can be solidified to form a first solidified free form layer 110. Solidifying can occur at a low temperature and can include at least one of solidifying via a low-temperature chemical reaction (e.g., a sol-gel reaction) and drying at a low temperature. As shown in FIG. 1, in some embodiments, some shrinkage can occur during the solidifying step.

In some embodiments, a "low temperature" can generally refer to a temperature of no greater than about 100° C., in some embodiments, no greater than about 90° C., in some embodiments, no greater than about 75° C., in some embodiments, no greater than about 50° C., in some embodiments, no greater than about 30° C., and in some embodiments, no greater than about 10° C. In some embodiments, a "low temperature" can refer to room temperature—about 25° C.

In some embodiments, the first free form layer 108 can be solidified by drying to at least partially remove a solvent or liquid. In some embodiments, the first free form layer 108 can be solidified via a chemical reaction (e.g., a sol-gel reaction) in which bonding (e.g., cross-linking) can occur to form a network. In some embodiments, both drying and a chemical reaction can occur to form the first solidified free form layer 110. In embodiments in which the first free form layer 108 is solidified but not necessarily dried, the first solidified free form layer 110 can still include moisture or be wet in subsequent machining steps (e.g., step 1D, described below), as long as the solidified free form layer 108 has a suitable strength.

In some embodiments, the solidified free form layer 108 can have a Vickers hardness of at least about 0.8, in some embodiments, at least about 1.0, and in some embodiments, at least about 1.5. In some embodiments, the solidified free form layer 108 can have a hardness of no greater than about 3.0, in some embodiments, no greater than about 2.5, and in some embodiments, no greater than about 2.0. In some embodiments, the solid free form layer 108 can have a Vickers hardness ranging from about 1.0 to about 1.8. Vickers hardness can be determined, for example, with a pyramid shaped diamond indenter and by application of 50 g weight.

As mentioned above, the solidified free form layers of the methods of the present disclosure are less dense than fired or sintered materials and the lower densities can facilitate machining of the solidified layer to a desired shape while reducing waste, reducing wear on machining tools, and/or decreasing the cycle time to produce a dental appliance.

In some embodiments employing drying as the mode of solidifying, a slurry can be used in which a sol-gel additive is not added. In addition, in some embodiments, a non-reactive binder can be added to the slurry to promote hardening to a suitable degree during the drying step. Any drying step of the present disclosure can be characterized by at least one of the following features:
  duration: up to about 8 h, up to about 1 h, up to about 30 minutes, or up to about 15 minutes,
  temperature: from about 10 to about 100° C., or about 20 to about 80° C., and/or
  pressure: ambient pressure.

During the drying step, the network-formation of the binder can be finalized and low boiling components that may have been generated during the network forming process, if any, can evaporate from the layer.

Drying can be performed at ambient conditions by simply letting the mixture making up the free form layer stand for a sufficient period of time. If a more rapid drying is desired, drying can be performed in a drying oven.

As further shown in FIG. 1, in a fourth step 1D, the first solidified free form layer 110 can be machined (e.g., according to a subtractive process) to a desired shape to form a first article 113 comprising a first shaped layer 112 and the solid structure 102. The term "article" is used by way of example only to indicate any article as defined above, but it should be understood that a variety of other terms, such as "construction," "intermediate," "workpiece," "dental workpiece," or the like, could instead be used to describe the form resulting from forming a layer having a desired shaped according to the methods of the present disclosure.

As schematically represented by the x, y and z axes in the fourth step 1D, the first solidified free form layer 110 can be machined in such a way that the first shaped layer 112 can include any desired three-dimensional shape. A machining tool 115 is shown for illustration purposes.

In some embodiments, the first shaped layer 112 can have a regular (e.g., cubic, cylindrical, etc.) or irregular shape (e.g., shape of a tooth, veneer, inlay, onlay, crown, bridge, orthodontic bracket, other suitable dental appliance shapes, etc., or combinations thereof). For example, a "simple, tooth-like" shape can be used for near-net shape applications. In some embodiments, a three-dimensional shape having a specially designed tooth-shape can be used for individual net-shape applications. As mentioned above, a specially designed tooth-shape can be produced by a digital workflow and subtractive CAD/CAM processes.

A machining step of the present disclosure can be characterized by at least one of the following features:
  machining can be accomplished under dry or wet conditions,
  milling parameter rotation: about 18,000 to about 32,000 rpm, and/or
  milling parameter motion: about 1,500 to about 2,500 mm per minute.

Other machining equipment as those mentioned in the above definition of machining can be used, if desired.

The method 100 can further include steps to form additional layers on the first shaped layer 112, following a similar layering and machining process. For example, in a fifth step 1E, a second slurry 116 can be applied onto (e.g., directly onto) the first shaped layer 112 to form a second free form layer 118, according to the same features, and alternatives thereto, described above with respect to the first application step. The second slurry 116 can be the same or a different formulation as that of the first slurry 106, depending on the desired layers, and the desired properties of each layer, of the resulting layered dental appliance. For example, in some embodiments, the first slurry 106 can include a formulation adapted to simulate a dentin layer, and the second slurry 116 can include a formulation adapted to simulate an enamel layer, and so on.

In a sixth step 1F of the method 100, the second free form layer 118 can be solidified to form a second solidified free form layer 120, according to the same features, and alternatives thereto, described above with respect to the first solidifying step. As shown in step 1F, some shrinkage can occur during solidification.

As further shown in FIG. 1, in a seventh step 1G, the second solidified free form layer 120 can be machined (e.g., according to a subtractive process) to a desired shape to form a second article 123 comprising a second shaped layer 122, the first shaped layer 112, and the solid structure 102. As shown in the seventh step 1G, the second shaped layer 122 can cover a substantial portion of the first shaped layer 112 but need not entirely cover or envelope the first shaped layer 112, depending on the desired structure and composition of the resulting layered dental appliance. Again, similar to step 1D, the x, y and z axes schematically represent that the second solidified free form layer 120 can be machined in such a way that the second shaped layer 122 can include any desired three-dimensional shape. A machining tool 125 is shown for illustration purposes. The second shaped layer 122 can include a different three-dimensional shape than the first shaped layer 112, such that the method 100 can be used to produce a layered dental appliance, where each layer forming the dental appliance can have an individual and unique shape and/or formulation. For example, each layer can have a unique color and/or transparency (or other optical or aesthetic properties), in addition to its unique shape.

The iterative layering and machining steps (e.g., steps 1E-1G) can then be repeated to form as many shaped layers as desired. As shown in step 1H, when the desired number of shaped layers has been produced, the final article (e.g., the second article 123 in the exemplary method 100 of FIG. 1) can be fired to form a layered dental appliance 130 comprising one or more fired and shaped layers. For example, in the embodiment illustrated in FIG. 1, the second article 123 is fired to form a first fired shaped layer 112' and a second fired shaped layer 122' on the solid structure 102. Such an additional firing step can be used to achieve the desired final density in the resulting layered dental appliance 130.

As shown in step 1H, shrinkage of at least the first fired shaped layer 112' and the second fired shaped layer 122' can occur as a result of the sintering step. To accommodate for any shrinkage that may occur, each individual layer that is formed can be machined to an enlarged version of the desired final layer. For example, in some embodiments step 1D, the first shaped layer 112 can actually be enlarged relative to the final desired shape of the first layer. Such an enlargement can be accomplished using the original data from the digital workflow and a CAD/CAM system.

The dental appliance 130 can then be used for its desired application, or the dental appliance 130 can be further processed, including, but not limited to, being further sintered, machined, etc., or combinations thereof.

In addition, in some embodiments, further processing of the dental appliance 130 can include removal of the solid structure 102, such that the resulting dental appliance 130 includes a dental veneer, for example, comprising the first fired shaped layer 112' and the second fired shaped layer 122'.

A firing or sintering step of the present disclosure, which is distinct from the low-temperature solidifying steps described above, can be characterized by at least one of the following features:

duration: about 10 to about 60 min or about 20 to about 25 min, temperature: about 600 to about 900° C. or about 750 to about 850° C., pressure: about 10 to about 50 mbar or about 15 to about 35 mbar, and/or atmosphere: air.

Sintering can be conducted in a commercially available sinter furnace (e.g. Austromat 3001 from Dekema Comp.; Germany). In some embodiments when sintering to full density is employed, the sintered material can have a density in a range of about 2 g/cm$^3$ to about 2.7 g/cm$^3$.

The sintered material can include a level of translucency. The translucency can be specified by the opacity of a material relative to daylight. In some embodiments, the opacity of the sintered material ranges from about 50% to about 60% (e.g., corresponding to natural dental enamel), in some embodiments from about 60% to about 80% (e.g., corresponding to natural dentine), and in some embodiments from about 80% to about 90% (e.g., corresponding to natural opaque dentine).

In some embodiments, the desired dental appliance can include only one layer formed over the solid structure 102. In such embodiments, the method 100 can include steps 1A-1D, and can further include firing the first article 113 to form the resulting dental appliance.

In some embodiments, the thickness of the various layers can vary. For example, in some embodiments, the thickness, color, translucency, and/or shape of each layer can be controlled to simulate a desired portion or layer of a natural tooth (e.g., dentin, enamel, etc.). In some embodiments, the thickness of the layers can generally increase from the outermost layer to the innermost layer (e.g., adjacent the solid structure 102). In some embodiments, the thickness of the layers can generally decrease from the outermost layer to the innermost layer.

In some embodiments, the resulting dental appliance (e.g., the dental appliance 130), or one or more layers of the dental appliance, may be substantially free of cells, voids or pores, or can include up to about 20 cells per mm$^2$. In some embodiments, the dental appliance, or one or more layers of the dental appliance can include about 4 to about 10 cells per mm$^2$. In some embodiments, the cells can have a diameter of less than about 150 μm, in some embodiments less than about 100 μm, and in some embodiments less than about 50 μm.

In some embodiments, the volume of the cells in the dental appliance (or one or more layers of the dental appliance), relative to the total volume of the dental appliance (or relative to the total volume of the one or more layers of the dental appliance) can range from about 20% to about 40%, and in some embodiments can range from about 30% to about 38%.

As can be understood by the above description of the method 100 of FIG. 1 and alternatives to the method 100, the present disclosure provides a multilayer dental appliance, wherein the innermost layer can include the dental core. Furthermore, the method 100 is shown by way of example only as including two layering and machining steps. However, it should be understood that as many layering and machining steps as necessary can be employed to form a layered dental appliance having a desired number of layers.

The following description of the formulation of the slurry and exemplary methods of forming one or more slurries of the present disclosure can generally apply to each of the first slurry 106 and the second slurry 116 shown in FIG. 1, as well as to additional slurries that may be necessary in another embodiment of the method of the present disclosure. Other details and aspects regarding the mixture or slurry can be found in US Patent Publication No. 2011/0151411, entitled "Dental Appliance, Process for producing a dental appliance and Use thereof," the disclosure of which is incorporated herein by reference in its entirety.

Liquid

The nature and structure of the liquid to be used in a slurry of the present disclosure is not particularly limited, unless the intended purpose cannot be achieved.

In some embodiments, the liquid can be characterized by at least one of the following features:
  boiling point: about 60 to about 120° C.,
  freezing point: about −120 to about 0° C., and/or
  density: about 0.7 to about 1.2 $g/cm^3$.

Specific examples of liquids include, but are not limited to, water, alcohols (including methanol, ethanol, n- and iso-propanol), ketones (including acetone), and combinations thereof.

In some embodiments, the liquid can be present in an amount ranging from about 15 wt.-% to about 60 wt.-%, in some embodiments from about 20 wt.-% to about 40 wt.-%, and in some embodiments from about 25 wt.-% to about 35 wt.-%, with respect to the whole composition or mixture, respectively.

In some embodiments, the liquid can be present in an amount of at least about 15 wt.-%, in some embodiments at least about 20 wt.-%, and in some embodiments at least about 25 wt.-%, with respect to the whole composition or mixture, respectively.

In some embodiments, the liquid can be present in an amount of no greater than about 35 wt.-%, in some embodiments no greater than about 40 wt.-%, and in some embodiments no greater than about 60 wt.-%, with respect to the whole composition or mixture, respectively.

Inorganic Binder

The nature and structure of the inorganic binder to be used in a slurry is not particularly limited, either, unless the intended purpose cannot be achieved.

The inorganic binder can form an inorganic network upon initiating a curing or hardening reaction. The curing or hardening reaction can be initiated, for example, by adjusting the pH value, either by adding acidic or basic reagents including those described in more detail below.

The network formed by the inorganic binder can have a similar or essentially identical chemical nature or composition as the chemical nature or composition of the glass/glass ceramic powder/particles used.

In some embodiments, the inorganic binder precursor can be a liquid at ambient conditions (e.g., 23° C.; 1013 mbar) or applied as an aqueous solution and can be characterized by at least one of the following features:
  density: about 0.7 to about 1.5 $g/cm^3$ or about 0.9 to about 1.4 $g/cm^3$,
  molecular mass: about 100 to about 500 g/mol or about 150 to about 250 g/mol (for molecular precursors),
  containing Si and O, and/or
  producing low boiling by—or condensation products during hardening, if any (e.g. boiling point below about 120° C.).

Specific examples of inorganic binder precursors include, but are not limited to tetra alkyl (e.g. C1 to C4) orthosilicates (including tetramethyl orthosilicate (TMOS), tetraethyl orthosilicate (TEOS)), water glass and silica sol.

In some embodiments, the inorganic binder (e.g., silica) can be present in an amount ranging from about 0.1 wt.-% to about 40 wt.-%, in some embodiments from about 1.0 wt.-% to about 20 wt.-%, and in some embodiments from about 2.0 wt.-% to about 10 wt.-%, with respect to the solids content of the mixture, respectively.

In some embodiments, the inorganic binder can be present in an amount of at least about 0.1 wt.-%, in some embodiments at least about 1.0 wt.-%, and in some embodiments at least about 2.0 wt.-%, with respect to the solids content of the mixture, respectively.

In some embodiments, the inorganic binder can be present in an amount no greater than about 10 wt.-%, in some embodiments no greater than about 20 wt.-%, and in some embodiments no greater than about 40 wt.-%, with respect to the solids content of the mixture, respectively.

Glass and/or Glass Ceramic Powder

The nature and structure of the glass and/or glass ceramic powder to be used in a slurry is not particularly limited, either, unless the intended purpose cannot be achieved.

The glass and/or glass ceramic powder may consist essentially of, or consist only of a glass and/or glass ceramic material. The glass and/or glass ceramic material can be selected to be compatible for use in human bodies. Furthermore, the glass and/or glass ceramic material can be selected to provide good aesthetic appearance for the dental appliance.

In some embodiments, the glass and/or glass ceramic powder can be characterized by at least one of the following features:
  mean particle size: range from about 5 μm to about 60 μm, or from about 10 to about 40 μm (measured with laser diffraction);
  melting temperature: around or less than 1000° C. and/or
  density: about 2.0 to about 2.6 or about 2.2 to about 2.5 $g/cm^3$ (according to the technical data sheet provided by the manufacturer).

In some embodiments, a glass composition, which can be used, can include:
  silica: about 60 to about 70 wt.-%,
  alumina: about 9 to about 13 wt.-%,
  potassium-oxide: about 5 to about 10 wt.-%,
  sodium-oxide: about 9 to about 13 wt.-%,
  lithium-oxide: about 0 to abut 1 wt.-%,
  calcium oxide: about 2 to about 5 wt.-%,
  barium-oxide: about 0 to about 2 wt.-% (optional),
  zirconium oxide: about 0 to about 1 wt.-% (optional), and
  cerium-oxide or cerium-fluoride: about 0 to about 1 wt.-% (optional).

Examples of glass and/or glass ceramic materials that can be used include those commercially available under the designations: "VM 9" from Vita Zahnfabrik, Bad Säckingen, Germany, "Cerabien Zr" from Noritake Inc., Japan, "Vintage" from Shofu, Japan; "ZIROX" from Wieland GmbH & Co.KG, Pforzheim, Germany and LM-$ZrO_2$ from Chemichl, Liechtenstein.

In some embodiments, the glass and/or glass ceramic powder can be present in an amount of at least about 40 wt.-%, in some embodiments at least about 60 wt.-%, and in some embodiments at least about 65 wt.-%, with respect to the whole composition or mixture, respectively.

In some embodiments, the glass and/or glass ceramic powder can be present in an amount no greater than about 75 wt.-%, in some embodiments no greater than about 80 wt.-%, and in some embodiments no greater than about 85 wt.-%, with respect to the whole composition or mixture, respectively.

In some embodiments, the glass and/or glass ceramic powder can be present in an amount ranging from about 40 wt.-% to about 85 wt.-%, in some embodiments ranging from about 60 wt.-% to about 80 wt.-%, and in some embodiments ranging from about 65 wt.-% to about 75 wt.-%, with respect to the whole composition or mixture, respectively.

The distribution of the particle size may be for example:
10% of the particles smaller than about 5 μm or smaller than about 2 μm;
50% of the particles smaller than about 25 μm or smaller than about 10 μm; and
90% of the particles smaller than about 70 μm or smaller than about 40 μm.

Additives

A mixture or slurry of the present disclosure can also comprise further components or additives, such as colorant(s) and/or pigments (e.g. traces of fluorescent, organic pigments e.g. for easier identification of the blocks ("labeling"), which can be burnt out during firing; and/or inorganic pigments that remain in the appliance for coloration of the sintered material). Such additives or components can also be present or included in the glass and/or glass ceramic powder or particles. Suitable colorants can include one or more of the following elements or ions thereof: Fe, Mn, V, Cr, Zn, Sn and Co.

Further additives, which can be added, can include retarders (such as 1,2-diphenylethylene); plasticizers (including polyethylene glycol derivatives, polypropylene glycols, low-molecular-weight polyesters, dibutyl, dioctyl, dinonyl and diphenyl phthalate, di(isononyl adipate), tricresyl phosphate, paraffin oils, glycerol triacetate, bisphenol A diacetate, ethoxylated bisphenol A diacetate, silicone oils, or a combination thereof); fluoride releasing materials; rheological modifiers (e.g., polyethyleneglycols; polysaccharides, such as xanthan gum, methyl cellulose, etc., or combinations thereof; or combinations thereof); or a combination thereof.

Some embodiments include no additives, however, if they are present, they can be present in an amount of at least about 0.01 wt.-%, in some embodiments at least about 0.1 wt.-%, and in some embodiments at least about 1 wt.-%, with respect to the whole composition or mixture, respectively.

In some embodiments, additives can be present in an amount no greater than about 20 wt.-%, in some embodiments no greater than about 10 wt.-%, and in some embodiments no greater than about 5 wt.-%, with respect to the whole composition or mixture, respectively.

In some embodiments, additives can be included in amounts ranging from about 0.01 to about 20 wt.-%, in some embodiments ranging from about 0.1 to about 10 wt.-%, and in some embodiments ranging from about 1 to about 5 wt.-%.

As long as the additive does not influence the sol-gel reaction, it can be employed in any desired amount with respect to the whole composition or mixture.

In some embodiments, a slurry or mixture to be used in the layering process of the present disclosure can include the individual components in the following amounts:
liquid: from about 15 wt.-% to about 60 wt.-%, or from about 20 wt.-% to about 40 wt.-%, or from about 25 wt.-% to about 35 wt.-%, with respect to the whole weight of the mixture;
inorganic binder: from about 0.1 wt.-% to about 40 wt.-%, or from about 1 wt.-% to about 20 wt.-%, or from about 2 wt.-% to about 10 wt.-%, with respect to the solids content of the mixture;
glass and/or glass ceramic powder: from about 40 wt.-% to about 85 wt.-%, or from about 60 wt.-% to about 80 wt.-%, or from about 65 wt.-% to about 75 wt.-%, with respect to the whole weight of the mixture; and
additives (including colorant(s) or rheological modifier(s)): from about 0.01 to about 20 wt.-%, or from about 0.1 to about 10 wt.-%, or from about 1 to about 5 wt.-%, with respect to the whole weight of the mixture.

In some embodiments, the ratio (with respect to weight) of liquid to inorganic binder can be in a range of about 20:1 to about 1:1, or from about 10:1 to about 3:1. If the ratio is outside this range, the obtained dental appliance may not include the desired properties.

In some embodiments, the ratio (with respect to weight) of inorganic binder to glass and/or glass ceramic powder can be in a range of about 1:100 to about 1:5, or from about 1:50 to about 1:10. If the ratio is outside this range, the obtained dental appliance may not include the desired properties.

Forming the Slurry

In some embodiments, the slurry or mixture can be obtained by the following exemplary process:
i) providing a liquid,
ii) adjusting the liquid to a pH value suitable to start the condensation reaction, depending on the binder precursor used (e.g. 10 to about 12 for TMOS or about 2 to about 4 for water glass and silica sol),
iii) adding the glass and/or glass ceramic powder, and
iv) adding the inorganic binder,
wherein steps iii) and iv) can also be carried out in reverse order.

The pH value can be adjusted by using conventional basic reagents like NaOH, KOH or $NH_3$ containing solutions or acidic reagents like HCl—, $HNO_3$—, and/or or acetic acid-containing solutions, wherein the pH value can be determined during the adjustment step. The pH value can be determined by e.g. pH sensitive paper or electronic equipment (e.g. pH electrode). If strong acids or bases are employed, determination of the pH value can also be obtained via calculation from the amount of acid used.

The inorganic binder can be added rapidly while the solution is stirred. The addition of the inorganic binder can mark the starting point of a sol-gel reaction caused by the reaction of the inorganic binder molecules. In some embodiments, a two-slurry system can be used. If a two-slurry system ("I" and "II") is used, mixing of the two slurries marks the starting point of the sol-gel reaction.

During the sol-gel reaction, an inorganic network can be formed.

In some embodiments, providing a slurry or mixture can be characterized by at least one of the following features:
time needed for gelation (i.e. time from adding the inorganic binder until solidification of the mixture to the point that it cannot be deformed or removed from the dental core by tilting or shaking); 30 seconds to 10 minutes; and/or
time needed for settling (i.e., time from stopping the mixture being stirred until the mixture becomes inhomogeneous because of settling of the glass and/or glass ceramic particles): 7 minutes to more than one week (values were obtained either without inorganic binder present or with binder present but at a pH value that inhibits gelation).

In some embodiments, the mixtures or slurries to be used in the process of the present disclosure may not contain polymerizable organic binder components like (meth)acrylate or epoxy groups containing components. That is, in some embodiments, the mixture can be essentially free of polymerizable organic binder components. An organic binder within the meaning of the invention is a binder, which consists of organic compounds that are added to strengthen the appliance or workpiece and cannot be thermally removed from the workpiece below a temperature of 200° C.

In some embodiments, the addition or presence of an initiator (e.g. photo or redox initiator) for starting the hardening process of the inorganic binder is typically not needed. The hardening process can be initiated by adjusting the pH value or simply by employing a diluted acidic/basic solution.

The production process of the present disclosure typically also does not include a pressing step (e.g. isostatic or uniaxial) or a pre-sintering step.

EMBODIMENTS

Embodiment 1 is a method for making a layered dental appliance, the method comprising:
  providing a dental core having a desired outer shape;
  applying a slurry to the dental core to form a first free form layer on the dental core;
  solidifying the first free form layer on the dental core; and
  machining the solidified first free form layer to a desired shape to form a first article comprising the dental core and a first shaped layer.

Embodiment 2 is the method of embodiment 1, wherein the dental core includes at least one of a ceramic, a metal, a metal alloy, a precious metal, a precious metal alloy, and a combination thereof.

Embodiment 3 is the method of embodiment 1, wherein the dental core is a fully sintered ceramic.

Embodiment 4 is the method of any of embodiments 1-3, wherein applying a slurry to the dental core to form a first free form layer includes forming a first free form layer having no prescribed outer shape.

Embodiment 5 is the method of any of embodiments 1-4, wherein the solidified first free form layer is not fired prior to being machined.

Embodiment 6 is the method of any of embodiments 1-5, further comprising repeating the applying, solidifying, and machining steps to form an article comprising n shaped layers on the dental core.

Embodiment 7 is the method of embodiment 6, further comprising firing the article to form a layered dental appliance.

Embodiment 8 is the method of any of embodiments 1-7, wherein the slurry is a first slurry, and further comprising:
  applying a second slurry to the first article to form a second free form layer;
  solidifying the second free form layer; and
  machining the solidified second free form layer to a desired shape to form a second article comprising the dental core, the first shaped layer and a second shaped layer.

Embodiment 9 is the method of embodiment 8, wherein the first slurry includes a different formulation than the second slurry.

Embodiment 10 is the method of embodiment 8 or 9, wherein applying a second slurry includes dipping the first article in the second slurry.

Embodiment 11 is the method of embodiment 8 or 9, wherein applying a second slurry includes decanting the slurry onto the first article.

Embodiment 12 is the method of embodiment 8 or 9, wherein applying a second slurry includes delivering the second slurry through a nozzle onto the first article.

Embodiment 13 is the method of any of embodiments 8-12, further comprising firing the second article to form a dental appliance comprising the dental core, a first fired shaped layer, and a second fired shaped layer.

Embodiment 14 is the method of embodiment 13, wherein the first layer is adapted to simulate a dentin layer, and wherein the second layer is adapted to simulate an enamel layer.

Embodiment 15 is the method of electromagnetic 13 or 14, wherein the second layer forms the outermost layer of the layered dental appliance.

Embodiment 16 is the method of any of embodiments 1-7, further comprising firing the first article to form a dental appliance comprising the dental core and a first fired shaped layer formed on the dental core.

Embodiment 17 is the method of any of embodiments 1-16, wherein applying a slurry includes dipping the dental core in the slurry.

Embodiment 18 is the method of embodiment 17, wherein dipping includes positioning at least a portion of the dental core in the slurry and removing the dental core from the slurry.

Embodiment 19 is the method of any of embodiments 1-16, wherein applying a slurry includes decanting the slurry onto the dental core.

Embodiment 20 is the method of any of embodiments 1-16, wherein applying a slurry includes delivering a slurry through a nozzle onto the dental core.

Embodiment 21 is the method of any of embodiments 1-20, further comprising rotating the dental core while the slurry is applied.

Embodiment 22 is the method of any of embodiments 1-21, further comprising activating the slurry prior to applying the slurry to the dental core.

Embodiment 23 is the method of any of embodiments 1-22, further comprising initiating a sol-gel reaction in the slurry prior to applying the slurry to the dental core.

Embodiment 24 is the method of any of embodiments 1-23, further comprising determining the desired shape of at least one of the dental core and the first shaped layer based on a digital workflow.

Embodiment 25 is the method of any of embodiments 1-7 and 16-24, wherein the first layer forms the outermost layer of the layered dental appliance.

Embodiment 26 is the method of any of embodiments 1-25, wherein the slurry includes at least one of a glass powder, a glass ceramic powder, and a combination thereof.

Embodiment 27 is the method of any of embodiments 1-26, wherein the slurry includes:
  (i) at least one of a glass powder and a glass ceramic powder;
  (ii) a liquid; and
  (iii) an inorganic binder.

Embodiment 28 is the method of embodiment 27, wherein the slurry further includes (iv) a rheological modifier.

Embodiment 29 is a method for making a layered dental appliance, the method comprising:
  providing a solid structure having a desired outer shape;
  applying a first slurry to the solid structure to form a first free form layer on the solid structure;
  solidifying the first free form layer on the solid structure;
  machining the solidified first free form layer to a desired shape to form a first article comprising the solid structure and a first shaped layer;
  applying a second slurry to the first article to form a second free form layer;
  solidifying the second free form layer on the first article; and machining the solidified second free form layer to a desired shape to form a second article comprising the solid structure, the first shaped layer and a second shaped layer.

Embodiment 30 is the method of embodiment 29, wherein the solid structure includes at least one of a dental core and a die.

Embodiment 31 is the method of embodiment 30, wherein the dental core includes at least one of a ceramic, a metal, a metal alloy, a precious metal, a precious metal alloy, and a combination thereof.

Embodiment 32 is the method of embodiment 30, wherein the dental core includes a fully sintered ceramic.

Embodiment 33 is the method of any of embodiments 29-32, wherein at least one of applying a slurry to the solid structure and applying a second slurry to the first article includes forming a free form layer having no prescribed outer shape.

Embodiment 34 is the method of any of embodiments 29-33, further comprising repeating the applying, solidifying, and machining steps to form an article comprising n shaped layers on the solid structure.

Embodiment 35 is the method of embodiment 34, further comprising firing the article to form a layered dental appliance.

Embodiment 36 is the method of any of embodiments 29-35, wherein the first slurry includes a different formulation than the second slurry.

Embodiment 37 is the method of any of embodiments 29-36, wherein at least one of applying a first slurry and applying a second slurry includes dipping.

Embodiment 38 is the method of any of embodiments 29-37, wherein at least one of applying a first slurry and applying a second slurry includes decanting the slurry.

Embodiment 39 is the method of any of embodiments 29-38, wherein at least one of applying a first slurry and applying a second slurry includes delivering the slurry through a nozzle.

Embodiment 40 is the method of any of embodiments 29-39, further comprising firing the second article to form a dental appliance comprising the solid structure, a first fired shaped layer, and a second fired shaped layer.

Embodiment 41 is the method of embodiment 40, wherein the solid structure is a dental core, and wherein the dental core forms a portion of the dental appliance.

Embodiment 42 is the method of embodiment 40, wherein the solid structure is a die, and further comprising removing the die from the layered dental appliance to form a layered veneer comprising the first fired shaped layer and the second fired shaped layer.

Embodiment 43 is the method of any of embodiments 40-42, wherein the first layer is adapted to simulate a dentin layer, and wherein the second layer is adapted to simulate an enamel layer.

Embodiment 44 is the method of any of embodiments 40-43, wherein the second layer forms the outermost layer of the layered dental appliance.

Embodiment 45 is the method of any of embodiments 29-44, further comprising rotating the solid structure while the first slurry is applied.

Embodiment 46 is the method of any of embodiments 29-45, further comprising activating at least one of the first slurry and the second slurry prior to applying the slurry.

Embodiment 47 is the method of any of embodiments 29-46, further comprising initiating a sol-gel reaction in at least one of the first slurry and the second slurry prior to applying the slurry.

Embodiment 48 is the method of any of embodiments 29-47, further comprising determining the desired shape of at least one of the solid structure, the first shaped layer, and the second shaped layer based on a digital workflow.

Embodiment 49 is the method of any of embodiments 29-48, wherein at least one of the solidified first free form layer and the solidified second free form layer is not fired prior to being machined.

Embodiment 50 is the method of any of embodiments 29-49, wherein at least one of the first slurry and the second slurry includes at least one of a glass powder, a glass ceramic powder, and a combination thereof.

Embodiment 51 is the method of any of embodiments 29-50, wherein at least one of the first slurry and the second slurry includes:
(i) at least one of a glass powder and a glass ceramic powder;
(ii) a liquid; and
(iii) an inorganic binder.

Embodiment 52 is the method of embodiment 51, wherein the slurry further includes (iv) a rheological modifier.

Embodiment 53 is the method of any of embodiments 1-52, wherein solidifying includes drying.

Embodiment 54 is the method of embodiment 53, wherein drying occurs at a temperature of no greater than about 100° C.

Embodiment 55 is the method of embodiment 53 or 54, wherein drying occurs at room temperature.

Embodiment 56 is the method of any of embodiments 1-55, wherein solidifying includes solidifying via a low-temperature chemical reaction.

Embodiment 57 is the method of embodiment 56, wherein the slurry includes a sol, and wherein the low-temperature chemical reaction includes a sol-gel reaction.

Embodiment 58 is the method of embodiment 56 or 57, wherein the low-temperature chemical reaction occurs at a temperature of no greater than about 100° C.

Embodiment 59 is the method of any of embodiments 56-58, wherein the low-temperature chemical reaction occurs at room temperature.

Embodiment 60 is the method of any of embodiments 1-59, wherein machining includes a subtractive CAD/CAM assisted process.

Embodiment 61 is the method of any of embodiments 1-60, wherein machining includes milling.

The following working examples are intended to be illustrative of the present disclosure and not limiting.

EXAMPLES

Example 1

Formation of a Dental Appliance Having a Single Veneer Layer

A Lawax block (from 3M ESPE, Seefeld, Germany) was milled in a LAVA CNC 500 (from 3M ESPE) to produce the outer shape of a typical incisor tooth stump. Excess wax was removed and the tooth stump was fixed to the Lawax frame with a plastic platelet.

A design for a zirconia dental core was made, so that the sintered core would fit onto the wax stump. LAVA zirconia was milled in a LAVA CNC 500 (from 3M ESPE) according to that design and sintered in a LAVA furnace (from 3M ESPE) at 1500° C. to form a zirconia dental core.

A slurry was prepared from 10.0 g of glass powder (GM/LM-Zr Incisal 2 from Chemichl, Liechtenstein) and 3.1 mL of deionized water. The slurry was stirred until the glass powder was distributed homogeneously. Then, 0.4 mL of TEOS (tetraethoxy silane, 98% from Fluka, Sigma-Aldrich, Germany) were added to the slurry. The vessel with the slurry was covered to avoid evaporation of solvent. The mixture was stirred until the TEOS phase disappeared.

A plastic spatula was used as a holder for the sintered zirconia dental core. The dental core was mounted on the spatula and dipped into the glass powder slurry. The dipping was repeated until a thick layer of slurry (at least 1 mm) coated the dental core. The slurry layer was dried first open to the air for about 5 minutes, then in a drying oven at 50° C. for about 30 minutes (drying oven from Memmert).

A design for a veneering was made, based on the design of the zirconia dental core. The dental core with the dried veneering slurry was mounted into the Lawax frame and the designed shape was milled into the veneering layer (LAVA CNC 500, from 3M ESPE). The milled restoration was then removed from the frame and sintered in a dental furnace (Austromat 3001 from Dekema, Germany) under vacuum at 770° C. for about 25 minutes. The result was a fully sintered dental restoration for a typical incisor.

Example 2

Formation of a Dental Appliance Having a Single Veneer Layer

Example 2 was performed following the same procedures as described above in Example 1, except that a different slurry formulation was used. A slurry was prepared of 10.0 g of glass powder (GM/LM-Zr Incisal 2 from Chemichl, Liechtenstein) and 3.3 mL of deionized water. The slurry was stirred until the glass powder was distributed homogeneously. Then, 0.4 mL of TMOS (tetramethoxy silane, 98% from Fluka, Sigma-Aldrich, Germany) were added to the slurry.

Example 3

Formation of a Dental Appliance Having Two Veneer Layers

A Lawax block (from 3M ESPE) was milled in a LAVA CNC 500 (from 3M ESPE) to produce the outer shape of a typical tooth stump fixed to a base of remaining wax. A zirconia dental core was made, so that the sintered core would fit onto the wax stump. LAVA zirconia was milled in a LAVA CNC 500 (from 3M ESPE) according to that design and sintered in a LAVA furnace (from 3M ESPE) at 1500° C. for about 3 hours. The sintered zirconia dental core was surface-treated for better adhesion by sandblasting with Rocatec Soft (from 3M ESPE) at 3 bar for a few seconds.

A first slurry was prepared of 10.0 g of glass powder (LM-Zr Dentin A4 from Chemichl, Liechtenstein), 1.6 mL of acetic acid (2 M, prepared with acetic acid (32%) from VWR, Germany and deionized water), 0.2 mL xanthan gum solution (0.33 wt.-%, prepared with xanthan gum from Jungbunzlauer, Switzerland and deionized water) and 0.7 mL silica sol (LEVASIL 300/30% from Obermeier, Germany). The slurry was stirred until the glass powder was distributed homogeneously. The slurry was put under vacuum with continued stirring for at least 5 minutes to remove air bubbles. The slurry was then filled into a syringe which can be capped to avoid evaporation of moisture from the slurry.

A plastic spatula was used as a holder for the sintered zirconia dental core. The dental core was mounted on the spatula, and the glass powder slurry was applied to the dental core constantly through the nozzle of the syringe until a layer of at least 1 mm thickness was obtained. The slurry was non-flowing and retained its position on the dental core. The slurry layer was dried first open to the air (no more than 5 minutes), then in a drying oven between 50° C. and 90° C., preferred at 70° C. (drying oven from Memmert), until it was completely dry, which took no more than 15 minutes.

A design for a veneering with two layers was made, based on the design of the zirconia dental core. The dental core with the dried veneering slurry was mounted into the Lawax frame and the designed shape of the first veneering layer was milled into the slurry layer (LAVA CNC 500 from 3M ESPE). The milled dental workpiece was then removed from the Lawax frame.

A second slurry was prepared according to the composition of the first slurry, but the glass powder was a different one (LM-Zr Incisal 4 from Chemichl, Liechtenstein). The complete procedure of the first slurry was repeated and the designed shape of the second veneering layer was milled into the second slurry layer. The milled dental workpiece was then removed from the Lawax frame.

The workpiece now consisted of a sintered zirconia dental core, a first layer of dentin mass in green state and a second layer of enamel mass in green state. The appliance was sintered in a dental furnace (Austromat 3001 from Dekema, Germany) under vacuum at 770° C. for about 25 minutes to produce a fully sintered dental restoration for a typical incisor.

The resulting dental restoration was an incisor-similar norm-geometry. Parts of the veneering turned white during firing (i.e., resulting in white spots). To avoid this, the present inventors would fire under an air atmosphere rather than under vacuum and/or would reduce the amount of acetic acid used (e.g., by ½ or ⅓). For example, a viable replacement slurry formulation would comprise: 1.1 mL deionized water, 0.6 mL acetic acid (2M), 0.2 mL xanthan solution, and 0.5 mL silica sol.

The embodiments described above and illustrated in the figure are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure. Various features and aspects of the present disclosure are set forth in the following claims.

What is claimed is:

1. A method for making a layered dental appliance, the method comprising:
   providing a dental core having a desired outer shape;
   providing a slurry comprising:
   (i) at least one of a glass powder and a glass ceramic powder, present in an amount of about 60 wt.-% to about 85 wt.-%;
   (ii) a liquid; and
   (iii) an inorganic binder precursor;
   applying the slurry to the dental core to form a first free form layer on the dental core;
   initiating a low-temperature chemical reaction in the slurry;
   solidifying the first free form layer on the dental core, wherein solidifying includes solidifying via the low-temperature chemical reaction; and
   machining the solidified first free form layer to a desired shape to form a first article comprising the dental core and a first shaped layer, wherein the solidified first free form layer is not fired prior to being machined.

2. The method of claim 1, wherein the dental core includes at least one of a ceramic, a metal, a metal alloy, a precious metal, a precious metal alloy, and a combination thereof.

3. The method of claim 1, wherein the dental core is a fully sintered ceramic.

4. The method of claim 1, further comprising firing the first article to form a layered dental appliance.

5. The method of claim 1, wherein applying a slurry includes dipping the dental core in the slurry.

6. The method of claim 1, wherein applying a slurry includes decanting the slurry onto the dental core.

7. The method of claim 1, wherein applying a slurry includes delivering a slurry through a nozzle onto the dental core.

8. The method of claim 1, further comprising rotating the dental core while the slurry is applied.

9. The method of claim 1, wherein initiating a low-temperature chemical reaction occurs prior to applying the slurry to the dental core.

10. The method of claim 1, wherein initiating a low-temperature chemical reaction in the slurry includes initiating a sol-gel reaction in the slurry.

11. The method of claim 1, wherein solidifying includes drying.

12. The method of claim 1, wherein the slurry includes a sol, and wherein the low-temperature chemical reaction includes a sol-gel reaction.

13. The method of claim 1, wherein the low-temperature chemical reaction occurs at a temperature of no greater than about 100° C.

14. The method of claim 1, wherein providing the slurry includes adjusting the liquid to a pH value suitable to initiate the low-temperature chemical reaction of the inorganic binder precursor, wherein the liquid is adjusted to a basic pH range when the inorganic binder precursor comprises a tetra alkyl orthosilicate, and wherein the liquid is adjusted to an acidic pH range when the inorganic binder precursor comprises water glass, silica sol, or a combination thereof.

15. The method of claim 1, wherein the slurry is essentially free of polymerizable organic binder components.

16. A method for making a layered dental appliance, the method comprising:
providing a solid structure having a desired outer shape;
providing a first slurry and a second slurry, each of the first slurry and the second slurry comprising:
(i) at least one of a glass powder and a glass ceramic powder, present in an amount of about 60 wt.-% to about 85 wt.-%;
(ii) a liquid; and
(iii) an inorganic binder precursor;
applying the first slurry to the solid structure to form a first free form layer on the solid structure;
initiating a reaction in the first slurry;
solidifying the first free form layer on the solid structure;
machining the solidified first free form layer to a desired shape to form a first article comprising the solid structure and a first shaped layer;
applying the second slurry to the first article to form a second free form layer;
initiating a reaction in the second slurry;
solidifying the second free form layer on the first article; and
machining the solidified second free form layer to a desired shape to form a second article comprising the solid structure, the first shaped layer and a second shaped layer,
wherein solidifying includes solidifying via a low-temperature chemical reaction,
wherein at least one of the solidified first free form layer and the solidified second free form layer is not fired prior to being machined.

17. The method of claim 16, wherein the solid structure includes at least one of a dental core and a die.

18. The method of claim 16, further comprising firing the second article to form a dental appliance comprising the solid structure, a first fired shaped layer, and a second fired shaped layer, wherein the second layer forms the outermost layer of the layered dental appliance.

19. The method of claim 16, wherein at least one of the first slurry and the second slurry further includes (iv) a rheological modifier.

20. The method of claim 16, wherein providing the first slurry and the second slurry includes adjusting the liquid to a pH value suitable to initiate the low-temperature chemical reaction of the inorganic binder precursor, wherein the liquid is adjusted to a basic pH range when the inorganic binder precursor comprises a tetra alkyl orthosilicate, and wherein the liquid is adjusted to an acidic pH range when the inorganic binder precursor comprises water glass, silica sol, or a combination thereof.

21. The method of claim 16, wherein the first slurry and the second slurry are each essentially free of polymerizable organic binder components.

* * * * *